US009701599B2

(12) United States Patent
Wang et al.

(10) Patent No.: US 9,701,599 B2
(45) Date of Patent: Jul. 11, 2017

(54) PROCESS FOR PRODUCING 2,3,3,3-TETRAFLUOROPROPENE

(71) Applicant: Honeywell International, Inc., Morris Plains, NJ (US)

(72) Inventors: Haiyou Wang, Amherst, NY (US); Hsueh Sung Tung, Getzville, NY (US); Selma Bektesevic, Williamsville, NY (US)

(73) Assignee: HONEYWELL INTERNATIONAL. INC., Morristown, NJ (US)

( * ) Notice: Subject to any disclaimer, the term of this patent is extended or adjusted under 35 U.S.C. 154(b) by 0 days.

(21) Appl. No.: 15/190,828

(22) Filed: Jun. 23, 2016

(65) Prior Publication Data

US 2016/0304420 A1 Oct. 20, 2016

Related U.S. Application Data

(63) Continuation of application No. 14/204,054, filed on Mar. 11, 2014, now abandoned.

(60) Provisional application No. 61/792,769, filed on Mar. 15, 2013.

(51) Int. Cl.
| | | |
|---|---|---|
| *C07C 17/25* | (2006.01) | |
| *C07C 17/20* | (2006.01) | |
| *C07C 17/087* | (2006.01) | |
| *B01J 27/125* | (2006.01) | |
| *B01J 23/75* | (2006.01) | |
| *B01J 27/128* | (2006.01) | |
| *B01J 23/26* | (2006.01) | |
| *B01J 23/745* | (2006.01) | |
| *B01J 23/755* | (2006.01) | |
| *B01J 27/10* | (2006.01) | |

(52) U.S. Cl.
CPC ............ *C07C 17/087* (2013.01); *B01J 23/26* (2013.01); *B01J 23/745* (2013.01); *B01J 23/75* (2013.01); *B01J 23/755* (2013.01); *B01J 27/10* (2013.01); *B01J 27/125* (2013.01); *B01J 27/128* (2013.01); *C07C 17/206* (2013.01); *C07C 17/25* (2013.01); Y02P 20/582 (2015.11)

(58) Field of Classification Search
CPC ... C07C 17/087; C07C 17/206; C07C 17/205; C07C 19/10; C07C 17/25; C07C 21/18; B01J 23/26
USPC .................................................. 570/160, 163
See application file for complete search history.

(56) References Cited

U.S. PATENT DOCUMENTS

| | | | |
|---|---|---|---|
| 2,931,480 A | 4/1960 | Marquis et al. | |
| 5,006,594 A | 4/1991 | Rees | |
| 5,162,594 A | 11/1992 | Krespan | |
| 6,340,773 B1 | 1/2002 | Zhang et al. | |
| 6,958,424 B1 | 10/2005 | Nair et al. | |
| 8,084,653 B2 | 12/2011 | Tung et al. | |
| 8,258,355 B2 | 9/2012 | Merkel et al. | |
| 2009/0240090 A1 | 9/2009 | Merkel et al. | |
| 2010/0036179 A1* | 2/2010 | Merkel ................ C07C 17/087 570/156 |
| 2010/0048961 A1 | 2/2010 | Merkel et al. | |
| 2010/0191150 A1 | 7/2010 | Palme, Jr. et al. | |
| 2011/0105820 A1 | 5/2011 | Harris | |
| 2011/0124930 A1 | 5/2011 | Smith et al. | |
| 2011/0160498 A1 | 6/2011 | Pigamo et al. | |
| 2011/0257636 A1 | 10/2011 | Whitman et al. | |
| 2012/0123173 A1 | 5/2012 | Hibino et al. | |
| 2012/0149951 A1 | 6/2012 | Mukhopadhyay et al. | |
| 2012/0178977 A1 | 7/2012 | Merkel et al. | |

FOREIGN PATENT DOCUMENTS

| | | |
|---|---|---|
| CN | 101522597 a | 9/2009 |
| CN | 102099319 A | 6/2011 |
| EP | 2 151 425 A2 | 2/2010 |
| EP | 2 374 782 A1 | 12/2011 |
| JP | 59201992 A | 4/1983 |
| WO | 2007794312 A2 | 7/2007 |
| WO | 2008040969 A2 | 4/2008 |

OTHER PUBLICATIONS

International Search Report and Written Opinion corresponding to PCT/US2014/025733, issued Jul. 17, 2014.
Banks, et al., "Preparation of 2,3,3,3-tetrafluoropropene from trifluoroacetylacetone and sulpher tetrafluoride"; Journal of Fluorine Chemistry 82, vol. 2 (1997), pp. 171-174.
First Office Action issued in Chinese Patent Application No. 201480016017.4 dated Jun. 24, 2016.
Supplementary European Search Report issued in Application No. 14 76 7400 dated Oct. 4, 2016.

* cited by examiner

*Primary Examiner* — Jafar Parsa
(74) *Attorney, Agent, or Firm* — Scully, Scott, Murphy & Presser, P.C.

(57) ABSTRACT

The invention relates to a process to prepare 2-chloro-3,3,3-trifluoropropene (HCO-1233xf) or 2-chloro-1,1,12-tetrafluoropropane (HCFC-244bb) using dichloro-trifluoropropanes and/or trichloro-difluoropropanes, and to prepare 2-chloro-3,3,3-trifluoropropene (HCO-1233xf) using various 242 and 243 isomers.

16 Claims, No Drawings

PROCESS FOR PRODUCING 2,3,3,3-TETRAFLUOROPROPENE

This application is a continuation under 35 USC §120 claiming benefit to U.S. Ser. No. 14/204,054 filed on Mar. 11, 2014, which claims benefit to provisional application U.S. Ser. No. 61/792,769 filed on Mar. 15, 2013, now abandoned.

FIELD OF THE INVENTION

The invention relates to a process to prepare 2-chloro-3,3,3-trifluoropropene (HCO-1233xf) or 2-chloro-1,1,12-tetrafluoropropane (HCFC-244bb) using dichloro-trifluoropropanes and/or trichloro-difluoropropanes, and to prepare 2-chloro-3,3,3-trifluoropropene (HCO-1233xf) using various 242 and 243 isomers.

BACKGROUND OF THE INVENTION

Certain hydrofluoroolefins (HFOs), such as tetrafluoropropenes (including 2,3,3,3-tetrafluoropropene (HFO-1234yf)), are now known to be effective refrigerants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike most chlorofluorocarbons (CFCs) and hydrochlorofluorocarbons (HCFCs), most HFOs pose no threat to the ozone layer. HFO-1234yf has also been shown to be a low global warming compound with low toxicity and, hence, can meet increasingly stringent requirements for refrigerants in mobile air conditioning. Accordingly, compositions containing HFO-1234yf is a leader among the materials being developed for use in many of the aforementioned applications.

Several methods of preparing HFOs are known. For example, U.S. Pat. No. 4,900,874 (Ihara et al) describes a method of making fluorine containing olefins by contacting hydrogen gas with fluorinated alcohols. Although this appears to be a relatively high-yield process, commercial scale handling of hydrogen gas at high temperature is potentially hazardous. Also, the cost of commercially producing hydrogen gas, such as building an on-site hydrogen plant, is economically costly.

U.S. Pat. No. 2,931,840 (Marquis) describes a method of making fluorine containing olefins by pyrolysis of methyl chloride and tetrafluoroethylene or chlorodifluoromethane. This process is a relatively low yield process and a very large percentage of the organic starting material is converted to unwanted and/or unimportant byproducts, including a sizeable amount of carbon black which tends to deactivate the catalyst used in the process.

The preparation of HFO-1234yf from trifluoroacetylacetone and sulfur tetrafluoride has been described (See Banks, et al., Journal of Fluorine Chemistry, Vol. 82, Iss. 2, p. 171-174 (1997)). Also, U.S. Pat. No. 5,162,594 (Krespan) discloses a process wherein tetrafluoroethylene is reacted with another fluorinated ethylene in the liquid phase to produce a polyfluoroolefin product.

Notwithstanding the above-noted process and other processes for producing fluorinated olefins in general and fluorinated propenes in particular, applicants have come to appreciate that a need remains for a more economically efficient means of producing hydrofluoroolefins in general and hydrofluoropropenes in particular, such as HFO-1234yf. The present invention satisfies this need among others.

SUMMARY OF THE INVENTION

It has been found that certain dichlorotrifluoropropane and trichlorodifluoropropane by-products produced in the manufacture of 2-chloro-3,3,3-trifluoropropene (HFO-1233xf) and 2-chloro-1,1,1,2-tetrafluoropropane (HCFC-244bb) can be further converted to the desired HFO-1233xf and/or HCFC-244bb product. Such dichlorotrifluoropropanes include, but are not limited to, 2,2-dichloro-1,1,1-trifluoropropane (HCFC-243ab), 2,3-dichloro-1,1,1-trifluoropropane (HCFC-243db), 1,2-dichloro-1,1,2-trifluoropropane (HCFC-243bc), and combinations thereof. Trichlorodifluoropropanes include, but are not limited to, 1,2,2-trichloro-1,1-difluoropropane (HCFC-242ac), 1,1,2-trichloro-1,2-difluoropropane (HCFC-242bc), 1,2,3-trichloro-1,1-difluoropropane (HCFC-24dc), and combinations thereof.

In one aspect, the present invention relates to a process for preparing 2-chloro-3,3,3,-trifluoropropene or 2-chloro-1,1,1,2-tetrafluoropropane that includes at least the following steps:

a. providing a feed stream comprising one or more dichlorotrifluoropropanes, such as 2,2l-dichloro-1,1,1-trifluoropropane (HCFC-243ab), 2,3-dichloro-1,1,1-trifluoropropane (HCFC-243db), 1,2-dichloro-1,1,2-trifluoropropane (HCFC-243bc), and combinations thereof; and/or one or more trichlorodifluoropropanes such as 1,2,2-trichloro-1,1-difluoropropane (HCFC-242ac), 1,1,2-trichloro-1,2-difluoropropane(HCFC-242bc), 1,2,3-trichloro-1,1-difluoropropane (HCFC-242dc), and combinations thereof, b. contacting the feed stream with anhydrous hydrogen fluoride in gas phase in the presence of a fluorination catalyst under conditions sufficient to produce a product stream comprising 2-chloro-3,3,3,-trifluoropropene and/or 2-chloro-1,1,1,2-tetrafluoropropane, and HCl, and c. isolating 2-chloro-3,3,3,-trifluoropropene and/or 2-chloro-1,1,1,2-tetrafluoropropane from the said product stream.

In another aspect, the present invention relates to a process for preparing 2-chloro-3,3,3-trifluoropropene by providing a starting composition including at least one compound of formula I, II, and/or III

$$CX_2=CCl-CH_2X \qquad (I)$$

$$CX_3-CCl=CH_2 \qquad (II)$$

$$CX_3-CHCl-CH_2X \qquad (III)$$

wherein X is independently selected from F, Cl, Br, and I, provided that at least one X is not fluorine. Such starting composition is contacted with a fluorinating agent to produce a final composition including 2-chloro-3,3,3-trifluoropropene (1233xf), HCl, unreacted HF, optional unreacted starting compound(s), and one or more by-products. The by-products may include one or a combination of trichlorofluoropropene (1231) isomers, 2,3-dichloro-3,3-difluoropropene (1232xf), 2-chloro-1,1,1,2-tetrafluoropropane (244bb), 1,1,1,2,2-pentafluoropropane (245cb), dichlorotrifluoropropanes (243), trichlorodifluoropropanes (242). The dichlorotrifluoropropanes and trichlorodifluoropropanes may include, but are not limited to, one or a combination of those compounds identified above or otherwise herein.

This final composition is then processed to separate desired products and recyclables from the remainder of the composition. In one aspect, 1233xf and HCl are first separated by feeding the composition into a recycle or distillation column. From such a column, the lighter components, such as 1233xf, 244bb (if any), 245cb (if any), HCl, and a portion of unreacted HF are isolated in a first or top stream, and the remaining organic components, such as unreacted HF, optional unreacted started compounds, one or more by-products (e.g. 242 and 243 isomers), and residual 1233xf are recovered in a second or bottom stream. From the top stream, 1233xf is purified using standard distillation methods, such as those provided herein. It is then forwarded to the second step of the reaction (discussed below) to produce 244bb and, ultimately, 1234yf.

The bottom stream of the recycle or distillation column is then further processed to isolate recyclable compounds from the first reaction step. Unreacted HF, for example, is substantially separated by phase separation. More specifically, the second or bottom stream from the recycle column is provided to a phase separator where unreacted HF separates into a first layer. In certain embodiments, this first layer also includes, as a residual portion, certain of the organics such as, but not limited to, 1233xf, 1232xf, and 243. The remaining organics (e.g. optional unreacted starting compound, residual 1233xf, and one or more by-products, which may include 1232xf, 242, and/or 243) are separated into a second layer. The HF-rich first layer is then extracted, optionally purified, and recycled. The second layer is similarly extracted and the unreacted starting material (if any) and recyclable products and/or by-products purified for recycling. In certain embodiments of the invention, the purified by-products preferably include at least one or more of the 242 and/or 243 isomers provided herein which are recycled to the first step fluorination reaction to produce 1233xf and/or 244bb.

In an alternative embodiment of the foregoing, the final composition of the reaction includes each of at least 2-chloro-3,3,3-trifluoropropene (1233xf), HCl, unreacted HF, optional unreacted starting compound, trichlorofluoropropene (1231) isomers, 2,3-dichloro-3,3-difluoropropene (1232xf), a first by-product selected from the group consisting of 1,1,1,2-tetrafluoropropane (244bb), 1,1,1,2,2-pentafluoropropane (245cb), and combinations thereof, and a second by-product selected from the group consisting of dichlorotrifluoropropane (243), trichlorodifluoropropane (242), and combinations thereof.

The final composition is then fed into a recycle or distillation column, where the lighter components, such as 1233xf, first by-product(s), HCl, and a portion of unreacted HF are isolated from the column in a first or top stream. The remaining components, such as unreacted HF, optional unreacted started compounds, residual 1233xf, trichlorofluoropropene (1231) isomers, 2,3-dichloro-3,3-difluoropropene (1232xf), second by-product(s) and third by-product(s) are recovered in a second or bottom stream.

From the top stream, the 1233xf is purified using standard methods, such as those described herein, and forwarded to the second stage of the reaction to produce 244bb.

The compounds in the bottom stream may then be further separated to isolate recyclable compounds from the first reaction step. Unreacted HF, for example, is separated by phase separation. More specifically, the second stream from the recycle column is provided to a phase separator where the majority of unreacted HF separates into a first layer. In certain embodiments, this first layer also includes, as a residual portion, certain of the organics such as, but not limited to, 1233xf, 1232xf, and 243. The remaining organics not provided in the first layer (e.g. optional unreacted starting compound, residual amounts of 1233xf, 1231 isomers, 1232xf, and second and third by-product(s)), and a small portion of unreacted HF) are separated into a second layer. The first layer, which is rich in HF, is then extracted, optionally purified, and recycled. With the second layer, the optional unreacted starting compound, trichlorofluoropropene (1231) isomers, 2,3-dichloro-3,3-difluoropropene (1232xf), second by-product(s) (e.g. 242 and/or 243) are separated from the third by-products by a high boiler purge system and are recycled. The optional unreacted starting compound, trichlorofluoropropene (1231) isomers, 2,3-dichloro-3,3-difluoropropene (1232xf), residual amounts of 1233xf and second by-product(s) may then be recycled to the reactor alone or in conjunction with the second by-products (e.g. 242 and/or 243).

It has been found that the separation of the components in the bottom stream of the first recycle column (e.g. HF, unreacted starting compound, and certain by-products, such as 242 and 243 isomers) allows for easier recycle of reactants back into reactor. The economy of the process is also improved by purifying such recycles and removing undesirable by-products that deleteriously affect catalyst life or otherwise degrade the reactor. To this end, the processes of the present invention result in reduced catalyst deactivation, as a result of the recycles, and corrosion of the reactor is minimized. The process to the present invention also result in higher reaction efficiency and reduction of waste by recycling unreacted and/or underfluorinated compounds, which are further converted into the desired products. To this end the present invention is further advantageous because it provides one or more process steps for improving the reaction efficiency used for the production of HFOs, such as 2-chloro-3,3,3,-trifluoropropene (1233xf) or, more broadly, for the production of 2,3,3,3-tetrafluoropropene (1234yf), of which 1233xf is a known intermediate. Additional embodiments and advantages to the present invention will be readily apparent to one of skill in the art, based on the disclosure provided herein.

In another aspect, it has found that in reacting 1233xf with HF to form 244bb, varying amounts of 243ab are formed as by-product. This is often particularly the case when a chloride such as HCl is a co-feed to this reaction. The unwanted generation of 243ab comes at the expense of 244bb yield. In another embodiment of the invention, 243ab formed in this regard, is converted to 1233xf which can be returned to the reaction to form 244bb. In one practice, the conversion of 243ab to 1233xf is by dehydrochlorination using select catalysts, such as carbon solids, metal halides, halogenated metal oxides, zero metals, and the like. In a preferred embodiment, the 243ab is dehydrochlorinated in the reaction whereby 244bb is converted to 1234yf. The 243ab is concurrently converted to 1233xf which can then be re-used as above.

In one embodiment, the invention is to a process to prepare 2-chloro-3,3,3-trifluoropropene (HCO-1233xf) or 2-chloro-1,1,12-tetrafluoropropane (HCFC-244bb) comprising contacting a compound selected from the group consisting of a dichloro-trifluoropropane, a trichloro-difluoropropane, and combinations thereof, with anhydrous hydrogen fluoride (HF) under conditions effective to produce 2-chloro-3,3,3-trifluoropropene (HCO-1233xf), 2-chloro-1, 1,12-tetrafluoropropane (HCFC-244bb), or combinations thereof. In one embodiment, the process is practiced with the proviso that 2,3-dichloro-1,1,1-trifluoropropane (HCFC-243db) is excluded from the dichloro-trifluoropropanes when preparing HCO-1233xf. In another embodiment, the invention is directed to process to prepare 2-chloro-1,1,12-tetrafluoropropane (HCFC-244bb) comprising contacting a compound selected from the group consisting of a dichloro-trifluoropropane, a trichloro-difluoropropane, and combinations thereof, with anhydrous hydrogen fluoride (HF) under conditions effective to produce HCFC-244bb.

In another embodiment, the invention is to a process to prepare 2-chloro-3,3,3-trifluoropropene (HCO-1233xf) and 2-chloro-1,1,1,2-tetrafluoropropane (244bb) comprising a contacting step comprising contacting at least one compound of Formulae (I), (II), (III)

CX$_2$=CCl—CH$_2$X (I)

CX$_3$—CCl=CH$_2$ (II)

CX$_3$—CHCl—CH$_2$X (III)

wherein X is independently selected from F, Cl, Br, and I, provided that at least one X is not fluorine, with anhydrous hydrogen fluoride (HF) in the presence of a catalyst under conditions effective to form a composition comprising HCO-1233xf and a by-product selected from the group consisting of a dichloro-trifluoropropane, a trichloro-difluoropropane and combinations thereof; recovering the by-product from the composition; recycling the by-product to the contacting step wherein the by-product is converted to 2-chloro-1,1,1,2-tetrafluoropropane (244bb).

In another embodiment, the invention is to a process to prepare 2-chloro-3,3,3-trifluoropropene (HCO-1233xf) comprising contacting 1,1,1-trifluoro-2,2-dichloropropane (243ab) with a dehydrochlorination catalyst under conditions effective to form 1233xf.

DETAILED DESCRIPTION OF THE INVENTION

According to one embodiment, the present invention relates to a manufacturing process for making 2,3,3,3-tetrafluoroprop-1-ene using a starting material according to any one or combination of formulas I, II, and/or III:

CX$_2$=CCl—CH$_2$X (Formula I)

CX$_3$—CCl=CH$_2$ (Formula II)

CX$_3$—CHCl—CH$_2$X (Formula III)

wherein X is independently selected from F, Cl, Br, and I, provided that at least one X is not fluorine. In certain embodiments, the compound(s) of Formula I, II and/or III contains at least one chlorine, a majority of the Xs as chlorine, or all Xs as chlorine. In certain embodiments, the compound(s) of formula I includes 1,1,2,3-tetrachloropropene (1230xa). In certain embodiments, the compound(s) of formula II includes 2,3,3,3-tetrachloropropene (1230xf). In further embodiments, the compound(s) of formula III include 1,1,1,2,3-pentachloropropane (240db).

The method generally includes at least three reaction steps. In the first step, a starting composition including compounds of Formula I, II, and/or III (e.g. 1,1,2,3-tetrachloropropene, 2,3,3,3-tetrachloropropene, and/or 1,1,1,2,3-pentachloropropane) is reacted with anhydrous HF in a first vapor phase reactor (fluorination reactor) to produce a mixture of 2-chloro-3,3,3-trifluoropropene (1233xf) and HCl. In certain embodiments, the reaction occurs in the vapor phase in the presence of a vapor phase catalyst, such as, but not limited to, a fluorinated chromium oxide. The catalyst may (or may not) have to be activated with anhydrous hydrogen fluoride HF (hydrogen fluoride gas) before use depending on the state of the catalyst.

While fluorinated chromium oxides are disclosed as the vapor phase catalyst, the present invention is not limited to this embodiment. Any fluorination catalysts known in the art may be used in this process. Suitable catalysts include, but are not limited to chromium, aluminum, cobalt, manganese, nickel and iron oxides, hydroxides, halides, oxyhalides, inorganic salts thereof and their mixtures and any one of which may be optionally fluorinated. Combinations of catalysts suitable for the present invention nonexclusively include $Cr_2O_3$, $FeCl_3/C$, $Cr_2O_3/Al_2O_3$, $Cr_2O_3/AlF_3$, $Cr_2O_3/$carbon, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. Chromium oxide/aluminum oxide catalysts are described in U.S. Pat. No. 5,155,082 which is incorporated herein by reference. Chromium (III) oxides such as crystalline chromium oxide or amorphous chromium oxide are preferred with amorphous chromium oxide being most preferred. Chromium oxide ($Cr_2O_3$) is a commercially available material which may be purchased in a variety of particle sizes. Fluorination catalysts having a purity of at least 98% are preferred. The fluorination catalyst is present in an excess but in at least an amount sufficient to drive the reaction.

This first step of the reaction may be conducted in any reactor suitable for a vapor phase fluorination reaction. In certain embodiments, the reactor is constructed from materials which are resistant to the corrosive effects of hydrogen fluoride and catalyst such as Hastalloy, Nickel, Incoloy, Inconel, Monel and fluoropolymer linings. If desired, inert gases such as nitrogen or argon may be employed in the reactor during operation.

When the compound of formula I is 1230xa, the mol ratio of HF to 1230xa in step 1 of the reaction is 1:1 to 50:1, from about 10:1 to about 50:1, or from about 10:1 to about 20:1. The reaction between HF and 1230xa is carried out at a temperature from about 150° C. to about 500° C., in certain embodiments, about 150° C. to about 400° C., or about 150° C. to about 300° C. The reaction pressure is about of about 0 psig to about 500 psig, in certain embodiments from about 20 psig to about 200 psig, or about 50 to about 100 psig.

Similarly, when the compound of formula II is 1230xf, the mol ratio of HF to 1230xf in step 1 of the reaction is 1:1 to 50:1, from about 10:1 to about 50:1, or from about 10:1 to about 20:1. The reaction between HF and 1230xf is carried out at a temperature from about 150° C. to about 500° C., in certain embodiments, about 150° C. to about 400° C., or about 150° C. to about 300° C. The reaction pressure is about of about 0 psig to about 500 psig, in certain embodiments from about 20 psig to about 200 psig, or about 50 to about 100 psig.

Similarly, when the compound of formula III is 240db, the mol ratio of HF to 240db in step 1 of the reaction is 1:1 to 50:1, from about 10:1 to about 50:1, or from about 10:1 to about 20:1. The reaction between HF and 240db is carried out at a temperature from about 150° C. to about 500° C., in certain embodiments, about 150° C. to about 400° C., or about 150° C. to about 300° C. The reaction pressure is about of about 0 psig to about 500 psig, in certain embodiments from about 20 psig to about 200 psig, or about 50 to about 100 psig.

The fluorination reaction may be carried out to attain a single- or multi-pass conversion of at least 1% or higher, 5% or higher, 10% or higher or about 20% or higher. In certain preferred embodiments of the present invention, the starting reagent is converted to 1233xf in a single pass, wherein the reaction conditions achieve a conversion amount greater than 75%, greater than 85%, greater than 95% or greater than 99%. To this end, the resulting effluent includes small or trace amounts of unreacted starting material or may be substantially free of such compounds.

The effluent from the fluorination reaction step, including any intermediate effluents that may be present in multi-stage reactor arrangements, are processed to achieve desired degrees of separation and/or other processing. For example, in embodiments in which the reactor effluent includes 1233xf, the effluent will generally also include HCl, unreacted HF, and trace amounts, if any, of unreacted starting component (e.g. 1230xa, 1230xf and/or 240db). The effluent may also include one or more by-product organics such as underfluorinated and/or overfluorinated intermediates. Non-limiting examples of underfluorinated intermediates include trichlorofluoropropene (1231) isomers and 2,3-dichloro-3,3-difluoropropene (1232xf), and non-limiting examples of overfluorinated intermediates include 2-chloro-1,1,1,2-tetrafluoropropane (244bb) and 1,1,1,2,2-pentafluoropropane (245cb). Other by-product organics may also include, but are not limited to, dichlorotrifluoropropane (243), and trichlorodifluoropropane (242).

In certain embodiments, the reaction by-products include one or more of dichlorotrifluoropropane and/or trichlorodifluororpropane by-products. Such dichlorotrifluoropropanes include, but are not limited to, one or more of the compounds 2,2-dichloro-1,1,1-trifluoropropane (HCFC-243ab), 2,3-dichloro-1,1,1-trifluoropropane (HCFC-243db), and 1,2-dichloro-1,1,2-trifluoropropane (HCFC-243bc). Trichlorodifluoropropanes include, but are not limited to, one or more of the compounds 1,2,2-trichloro-1,1-difluoropropane (HCFC-242ac), 1,1,2-trichloro-1,2-difluoropropane (HCFC-242bc), and 1,2,3-trichloro-1,1-difluoropropane (HCFC-242dc).

The effluent may be processed in one or more steps to isolate the 1233xf, as well as certain unreacted components and/or byproducts that are useful as a recyclables (including, but not limited to, the 242 and 243 isomers). Such isolation steps include those known in the art, and include without limitation, those described in U.S. Pat. Nos. 8,258,355 and 8,084,653 the entire contents of which are incorporated herein by reference. In one embodiment, a first recycle column, such as a distillation column is provided. The lighter components of the effluent are isolated from the top of the first recycle column and cooled and include, one or more of HCl, 1233xf, 244bb (if any), 245cb (if any) and a portion of unreacted HF. The remaining compounds are collected at the bottom stream of the column and include a bulk of the unreacted HF, trace amounts of unreacted starting component (if any), residual 1233xf and one or more of the by-product organics discussed herein. When referring to the bottom stream of the column, a "residual" amount of 1233xf refers to less than about 30 wt %, less than about 20%, less than about 15%, or less than about 10% of the total weight of the components in the bottom stream.

Each of the top stream and bottom stream are then independently processed. The top stream, for example, is first fed into an HCl column for HCl removal. High purity HCl is isolated from the top of the column and fed to an HCl recovery system. By way of non-limiting example, in such a recovery system HCl from the top stream may be absorbed in de-ionized water as concentrated HCl which, optionally, can be recovered for later sale. The remaining components, including 1233xf, 244bb (if any), 245cb (if any), and HF, exit the bottom of the HCl column and are further processed. In certain embodiments, this bottom stream is then provided to an HF recovery system to recover HF. The 1233xf/HF stream is fed to a sulfuric acid extractor or a phase separator for removal of HF from this mixture, i.e. the HF is either dissolved in sulfuric acid or phase separated from the organic mixture. With the former, HF is desorbed from the sulfuric acid/HF mixture by heating and distillation and recycled back to the reactor. In the case where a phase separator is used, HF is phase-separated using standard methods, such as those discussed below, and recycled back to the reactor. The organic either from the overhead of the sulfuric acid extractor or from the bottom layer of the phase separator is fed to the hydrofluorination reactor of Step (2), discussed below.

Components within the bottom stream of the first recycle column are separated, in certain embodiments, by phase separation. More specifically, the mixture is provided to a cooler and then to a phase separator where unreacted HF separates into an HF-rich first or top layer and an organic rich bottom or second layer. Any pressure which maintains the mixture substantially in the liquid phase may be employed. To this end, the pressure and temperature of the mixture may be adjusted such that the mixture remains substantially in the liquid phase. In certain embodiments, the HF-rich layer also includes, as a residual portion, certain of the organics such as, but not limited to 1233xf, 1232xf and 243. The remaining organics not provided in the first layer (particularly unreacted starting compound(s) (if any), residual 1233xf, 242 isomers, 243 isomers and dimers) separate into the organic-rich second or bottom layer. (When referring to the top layer, a "residual portion" of organics refers to less than about 50 wt %, less than about 40%, less than about 30%, less than about 20%, or less than about 10% of the total weight of the components in the top layer.) Phase separation may be performed at any combination of temperature and pressure such that two distinct liquid phases are formed in the phase separator. Phase separation may be carried out between about −30° C. to 60° C., preferably between about 0° C. and 40° C. and more preferably between about 10° C. and 30° C.

The HF rich layer is then isolated, such as by an HF phase pump, optionally purified, and recycled back to the reactor via a vaporizer. In one embodiment, the HF-rich layer is distilled to remove any moisture buildup or is isolated by single stage flash distillation. In another embodiment, before the recycle of HF-rich stream moisture (if any) is removed by injecting a chemical reagent such as $COCl_2$ (or $SOCl_2$) into said stream, which reacts with moisture to form $CO_2$ (or $SO_2$) and HCl. In even further embodiments, the HF-rich layer may be purified to remove the residual organics or may be recycled with the organics.

The organic-rich layer is also isolated, such as by an organic phase pump, then further processed to separate and purify the unreacted starting reactants (if any) and recyclable intermediates or by-products. In certain embodiments, the organic-rich layer is provided to a high boiler purge system, where unreacted starting reagents (if any), residual 1233xf, 1231 isomers, 1232xf, 243 isomers, 242 isomers, etc. are recovered and undesirable by-products are removed. (When referring to the organic-rich layer, a "residual" amount of HF refers to less than about 15 wt %, less than about 10%, less than about 5%, or less that about 3% of the total weight of the components in the bottom layer.) The high boiler purge system may be a distillation system operated in batch or continuous mode, preferably batch for operational reasons. Another option is to use a flash or series of flashes. In either case (distillation or flash), the more volatile components are recovered and recycled while the heavier components are removed from the system.

It has been found that the separation of the components in the bottom stream of the first recycle column into two phases allows for easier recycle of reactants back into reactor, and that the economy of the process is improved by using phase separator followed by purification of one or both layers before recycling. A presence of moisture in the feed, for example, leads to catalyst deactivation and corrosion of equipment and piping. Such moisture, if present, will typically concentrate in the HF-rich layer during phase separation. Accordingly, by purifying the HF-rich layer post-isolation, the moisture may be removed and the catalyst deactivation and corrosion minimized.

Removal of the high boiling point by-products and impurities is similarly advantageous because such compounds also cause catalyst deactivation if recycled. During phase separation, as set forth above, such compounds tend to concentrate in organic layer. Accordingly, post-isolation, the organic layer can also be purified in accordance with the foregoing to remove such compounds and isolate only those compound that are recyclable. Removal of the high boiling point compounds results in improved catalyst life and minimal purge streams.

In the second step of the process for forming 2,3,3,3-tetrafluoroprop-1-ene, the purified 1233xf intermediate stream is converted to 2-chloro-1,1,1,2-tetrafluoropropane (244bb). In one embodiment, this step may be performed in the liquid phase in a liquid phase reactor, which may be TFE or PFA-lined. Such a process may be performed in a temperature range of about 70-120° C. and about 50-120 psig.

Any liquid phase fluorination catalyst may be used in the invention. A non-exhaustive list include Lewis acids, transition metal halides, transition metal oxides, Group IVb metal halides, Group Vb metal halides, or combinations thereof. Non-exclusive examples of liquid phase fluorination catalysts are an antimony halide, a tin halide, a tantalum halide, a titanium halide, a niobium halide, and molybdenum halide, an iron halide, a fluorinated chrome halide, a fluorinated chrome oxide or combinations thereof. Specific non-exclusive examples of liquid phase fluorination catalysts are $SbCl_5$, $SbCl_3$, $SbF_5$, $SnCl_4$, $TaCl_5$, $TiCl_4$, $NbCl_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, or combinations thereof. Antimony pentachloride is most preferred.

These catalysts can be readily regenerated by any means known in the art if they become deactivated. One suitable method of regenerating the catalyst involves flowing a stream of chlorine through the catalyst. For example, from about 0.002 to about 0.2 lb per hour of chlorine can be added to the liquid phase reaction for every pound of liquid phase fluorination catalyst. This may be done, for example, for from about 1 to about 2 hours or continuously at a temperature of from about 65° C. to about 100° C.

This second step of the reaction is not necessarily limited to a liquid phase reaction and may also be performed using a vapor phase reaction or a combination of liquid and vapor phases, such as that disclosed in U.S. Published Patent Application No. 20070197842, the contents of which are incorporated herein by reference. To this end, the 1233xf containing feed stream is preheated to a temperature of from about 50° C. to about 400° C., and is contacted with a catalyst and fluorinating agent. Catalysts may include standard vapor phase agents used for such a reaction and fluorinating agents may include those generally known in the art, such as, but not limited to, hydrogen fluoride.

In this second step of the reaction, it is found that 243ab may be formed in varying degrees as a by-product. This is often particularly the case when a chloride such as HCl is a co-feed to this reaction. The unwanted generation of 243ab comes at the expense of 244bb yield. In one aspect of the invention, the 243ab thus formed is converted to 1233xf by catalytic dehydrochlorination. The 1233xf obtained by this conversion can be recycled back to the second step of the reaction or used for other purposes. In one embodiment, the 243ab is separately converted to recyclable 1233xf, subject to removal of 243ab from the product mixture of the second step of the reaction, as known in the art. Preferably, the 243ab is sent to the third step of the reaction, discussed hereunder, whereby it is dehydrochlorinated to form 1233xf as part of the process to dehydrochlorinate 244bb to 1234yf. Conveniently, the same reactor, catalysts, and conditions may be employed. The 1233xf thus obtained can be separated to the extent necessary as known in the art, and can be recycled back to the second step of the reaction whereby 244bb is generated, or it can be used otherwise.

In the third step of 1234yf production, the 244bb is fed to a second vapor phase reactor (dehydrochlorination reactor) to be dehydrochlorinated to make the desired product 2,3,3,3-tetrafluoroprop-1-ene (1234yf). This reactor contains a catalyst that can catalytically dehydrochlorinate HCFC-244bb to make HFO-1234yf.

In another aspect of the invention, the 244bb that is fed to the third step of 1234yf production process further comprises all or part of the 243ab that may have formed in the second step of the reaction. The reactor and catalyst suitable for dehydrochlorinating 244bb to 1234yf in this third step can also act to dehydrochlorinate 243ab to 1233xf, which can be optionally reused via recycle.

The catalysts may be metal halides, halogenated metal oxides, neutral (or zero oxidation state) metal or metal alloy, or activated carbon in bulk or supported form. Metal halide or metal oxide catalysts may include, but are not limited to, mono-, bi-, and tri-valent metal halides, oxides and their mixtures/combinations, and more preferably mono-, and bi-valent metal halides and their mixtures/combinations. Component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and $I^-$. Examples of useful mono- or bi-valent metal halide include, but are not limited to, LiF, NaF, KF, CsF, $MgF_2$, $CaF_2$, LiCl, NaCl, KCl, and CsCl. Halogenation treatments can include any of those known in the prior art, particularly those that employ HF, $F_2$, HCl, $Cl_2$, HBr, $Br_2$, HI, and $I_2$ as the halogenation source.

When neutral, i.e., zero valent, metals, metal alloys and their mixtures are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Inconel 825, Inconel 600, and Inconel 625. Such catalysts may be provided as discrete supported or unsupported elements and/or as part of the reactor and/or the reactor walls.

Preferred, but non-limiting, catalysts include activated carbon, stainless steel (e.g. SS 316), austenitic nickel-based alloys (e.g. Inconel 625), nickel, fluorinated 10% CsCl/MgO, and 10% $CsCl/MgF_2$. The reaction temperature is preferably about 300-550° C. and the reaction pressure may be between about 0-150 psig. The reactor effluent may be fed to a caustic scrubber or to a distillation column to remove the by-product of HCl to produce an acid-free organic product which, optionally, may undergo further purification using one or any combination of purification techniques that are known in the art.

The aforementioned catalysts for dehydrochlorination of 244bb to 1234yf are also useful for dehydrochlorination of 243ab to 1233xf, including in practices where this latter dehydrochlorination occurs in the third step of the reaction, as preferred, or is separately performed.

What is claimed is:

1. A process to prepare 2-chloro-1,1,1,2-tetrafluoropropane (HCFC-244bb) comprising contacting a compound selected from the group consisting of a dichloro-trifluoropropane, a trichloro-difluoropropane, and combinations thereof, with anhydrous hydrogen fluoride (HF) under conditions effective to produce HCFC-244bb, in the presence of a fluorination catalyst consisting of the group consisting of metal oxide, metal hydroxide, metal halide, metal oxyhalide, and mixtures thereof, wherein the metal is selected from the group consisting of chromium, aluminum, cobalt, manganese, nickel and iron and mixtures thereof.

2. The process of claim 1 wherein the dichloro-trifluoropropane is selected from the group consisting of 2,2-dichloro-1,1,1-trifluoropropane (HCFC-243ab), 1,2-dichloro-1,1,2-trifluoropropane (HCFC-243bc), 2,3-dichloro-1,1,1-trifluoropropane (HCFC-243db) and combinations thereof.

3. The process of claim 1 wherein the process occurs in a vapor phase.

4. The process of claim 1 wherein the catalyst is selected from the group consisting of $Cr_2O_3$, $FeCl_3/C$, $Cr_2O_3/Al_2O_3$, $Cr_2O_3/AlF_3$, $Cr_2O_3/carbon$, $CoCl_2/Cr_2O_3/Al_2O_3$, $NiCl_2/Cr_2O_3/Al_2O_3$, $CoCl_2/AlF_3$, $NiCl_2/AlF_3$ and combinations thereof.

5. The process of claim 1 wherein the contacting occurs at a temperature between about 150° C. and about 500° C.

6. The process of claim 1 wherein the contacting occurs at a pressure of between about 20 psig and about 200 psig.

7. A process to prepare 2-chloro-1,1,1,2-tetrafluorpropane (244bb) comprising contacting 2-chloro-3,3,3-trifluoropropene (HCO-1233xf) with HF in a reaction zone under conditions effective to form a composition comprising 244bb and 1,1,1-trifluoro-2,2-dichloropropane (243ab); contacting the 243ab with a dehydrochlorination catalyst selected from the group consisting of carbon solids, metal halides, halogenated metal oxides, zero metals and combinations thereof under conditions effective to form 1233xf; and recycling the formed 1233xf to the reaction zone.

8. The process of claim 1 wherein the trichloro-difluoropropane is selected from the group consisting of 1,2,2-trichloro-1,1-difluoropropane (HCFC-242ac), 1,1,2-trichloro-1,2-difluoropropane (HCFC-242bc), 1,2,3-trichloro-1,1-difluoropropane (HCFC-242dc) and combinations thereof.

9. A process to prepare 2-chloro-1,1,1,2-tetrafluoropropane (HCFC-244bb) comprising contacting a compound selected from the group consisting of a trichloro-difluoropropane, and combinations thereof, with anhydrous hydrogen fluoride (HF) under conditions effective to produce HCFC-244bb, wherein the trichloro-difluoropropane is selected from the group consisting of 1,2,2-trichloro-1,1-difluoropropane (HCFC-242ac), 1,1,2-trichloro-1,2-difluoropropane (HCFC-242bc), 1,2,3-trichloro-1,1-difluoropropane (HCFC-242dc) and combinations thereof.

10. The process of claim 9 wherein the process occurs in a vapor phase.

11. The process of claim 9 wherein the contacting occurs in the presence of a catalyst.

12. The process of claim 9 wherein the catalyst is selected from the group consisting of $Cr_2O_3$, $FeCl_3/C$, $Cr_2O_3/Al_2O_3$, $Cr_2O_3/AlF_3$, $Cr_2O_3/carbon$, $CoCl_2/Cr_2O_3/Al_2O_3$, $NiCl_2/Cr_2O_3/Al_2O_3$, $CoCl_2/AlF_3$, $NiCl_2/AlF_3$ and combinations thereof.

13. The process of claim 9 wherein the contacting occurs at a temperature between about 150° C. and about 500° C.

14. The process of claim 9 wherein the contacting occurs at a pressure of between about 20 psig and about 200 psig.

15. A process to prepare 2-chloro-1,1,1,2-tetrafluoropropane (HCFC-244bb) which comprises contacting 2-chloro-3,3,3-trifluoropropene (HCO-1233x) with HF in a first reaction zone under conditions effective to form a composition comprising 244bb and dichlorotrifluoropropane 243 isomer and recycling the dichlorotrifluoropropane 243isomer to a second reaction zone wherein said dichlorotrifluoropropane 243 isomer is contacted with HF under effective conditions to form 2-chloro-3,3,3-trifluoropropane and contacting 2-chloro-3,3,3-trifluoropropane with HF in the presence of a fluorination catalyst under conditions effective to form 2-chloro-1,1,1,2-tetrafluoropropane.

16. The process according to claim 15 wherein s dichlorotrifluoropropane 243 isomer is 2,3-dichloro-1,1,1-trifluoropropane.

* * * * *